(12) United States Patent
Yonish

(10) Patent No.: US 7,250,100 B2
(45) Date of Patent: Jul. 31, 2007

(54) TWO DIMENSIONAL ELECTROPHORESIS CASSETTE

(75) Inventor: Bryan Aaron Yonish, Durham, NC (US)

(73) Assignee: Duke University, Durham, NC (US)

( * ) Notice: Subject to any disclaimer, the term of this patent is extended or adjusted under 35 U.S.C. 154(b) by 358 days.

(21) Appl. No.: 10/462,910

(22) Filed: Jun. 17, 2003

(65) Prior Publication Data

US 2004/0256233 A1 Dec. 23, 2004

(51) Int. Cl.
*G01N 27/453* (2006.01)

(52) U.S. Cl. ............................ 204/610; 204/606
(58) Field of Classification Search ............... 204/456, 204/459, 606, 610
See application file for complete search history.

(56) References Cited

U.S. PATENT DOCUMENTS

| | | | | |
|---|---|---|---|---|
| 3,719,580 A | * | 3/1973 | Roberts et al. | 204/619 |
| 4,874,490 A | | 10/1989 | Hochstrasser | |
| 4,874,491 A | * | 10/1989 | Stalberg | 204/466 |
| 4,883,597 A | * | 11/1989 | Perlman | 210/640 |
| 5,064,769 A | * | 11/1991 | Gambert et al. | 436/516 |
| 5,407,546 A | | 4/1995 | Schickle | |
| 5,773,645 A | | 6/1998 | Hochstrasser | |
| 5,840,169 A | * | 11/1998 | Andersen | 204/462 |
| 6,013,165 A | * | 1/2000 | Wiktorowicz et al. | 204/456 |
| 2002/0100690 A1 | | 8/2002 | Herbert | |

FOREIGN PATENT DOCUMENTS

WO 02/26773 4/2002

OTHER PUBLICATIONS

Gorg et al, Electrophoresis 2000, 21, 1037-1053.*
Cockerill, Analytical Biochemistry, 168, pp. 451-454 (1988).*
*Ready Strip IPG Strips, Instruction Manual*, Catalog No. 163-2099, Bio-Rad Laboratories, Hercules, CA (date unavailable).
*2-D Electrophoresis for Proteomics, A Methods and Product Manual*, Bulletin 2651, Bio-Rad Laboratories, Inc. (date unavailable).

* cited by examiner

*Primary Examiner*—Kaj K. Olsen
(74) *Attorney, Agent, or Firm*—Myers Bigel Sibley & Sajovec

(57) ABSTRACT

A device for two-dimensional electrophoresis includes a cassette comprising two opposing plates. The two opposing plates form a first elongated portion for receiving a first elongated electrophoretic separation medium and a second portion extending away from the first portion. A second electrophoretic separation medium is on the second portion and between the two opposing plates. A dialysis membrane extends across the second electrophoretic separation medium.

12 Claims, 5 Drawing Sheets

TWO DIMENSIONAL ELECTROPHORESIS CASSETTE

BACKGROUND OF THE INVENTION

The present invention relates to the field of performing two-dimensional electrophoresis.

Electrophoresis using 2-D PAGE (Two-dimensional Poly-Acrylamide Gel Electrophoresis) techniques can separate proteins in a sample according to isoelectric pH (IpH) and molecular weight. Two-Dimensional PAGE generally provides isoelectric focusing electrophoresis in one direction followed by polyacrylamide gel electrophoresis in a second direction, and can be useful in analyzing the protein composition of a sample solution such as a biological sample. For example, gene activity may be studied by analyzing various proteins important to certain cellular functions.

For example, isoelectric focusing can use Immobilized pH gradient (IPG) strips to separate proteins based on their respective IpH values. An IpH is the pH value at which a protein carries no net charge and will not migrate in an electric field. An IPG strip with zwitter ionic peptides fixed to its surface can establish an identifiable pH gradient when a voltage is applied to electrodes on opposite sides of the IPG strip. Therefore, when a protein sample is applied to an IPG strip, each protein in the sample travels through the IPG strip until it reaches its IpH value on the IPG strip.

After proteins from the sample are focused on the IPG strip, a buffer, such as a buffer including SDS (sodium dodecyl sulfate), can be applied in preparation for polyacrylamide gel electrophoresis. Sodium dodecyl sulfate is a detergent that can solubize proteins to generate a uniform negative charge. Therefore, the SDS buffer disrupts hydrophobic interactions, increases the solubility of the protein, and leaves the protein molecules negatively charged. As a result, when the proteins are exposed to a polyacrylamide gel to which an electric current is applied, the proteins travel through the polyacrylamide gel and are separated according to their molecular weight. The polyacrylamide gel is typically a flat planar gel slab supported by a cassette housing.

After completion of the isoelectric focusing in one direction and PAGE in a second direction, the polyacrylamide gel has concentrations of protein deposits that are separated by IpH in one direction and molecular weight in the other direction. In order to view the resulting protein deposits, the polyacrylamide gel can be stained, for example, by removing the gel from its cassette housing and applying a staining reagent such as a silver or ruby protein stain.

Despite producing highly resolved results, 2-D PAGE presents technical challenges that may result in low reproducibility of results. The number of manual steps involved in 2-D PAGE may require a high level of operator skill to produce reliable 2-D PAGE results. In addition to being a labor-intensive process, many technical difficulties can be caused by operator inconsistencies. For example, the isoelectric focusing steps and the polyacrylamide electrophoresis steps are often carried out using separate devices, which may introduce poor reproducibility due to operator inconsistencies. U.S. Patent Application Publication No. 2002/0100690 to Herbert (hereinafter "Herbert"), disclosure of which is hereby incorporated by reference in its entirety, proposes a method in which the IPG strip and an agarose gel slab are carried on a single cassette. Increased automation of the 2-D PAGE steps may improve reproducibility of results and decrease the need for highly skilled operators.

SUMMARY OF THE INVENTION

Methods, systems, and devices for electrophoresis are provided that may address some of the challenges discussed above. Embodiments of the present invention provide a device for two-dimensional electrophoresis including a cassette comprising two opposing plates. The two opposing plates form a first elongated portion for receiving a first elongated electrophoretic separation medium and a second portion extending away from the first portion. A second electrophoretic separation medium is on the second portion and between the two opposing plates. A dialysis membrane extends across the second electrophoretic separation medium.

In some embodiments, the second electrophoretic separation medium can be deposited on one of the plates, and the dialysis membrane can define a void between the dialysis membrane and the other of the two opposing plates. The void can be used to inject fluids onto the electrophoretic separation media without requiring that the electrophoretic separation media be removed from the cassette.

In other embodiments, a loading chamber for an electrophoresis device is provided comprising a sample chamber having and opening configured to release a sample solution from the sample chamber into an cassette. A hydration chamber is adjacent the sample chamber, and a semi-permeable membrane is between the sample chamber and the hydration chamber. The membrane allows osmotic diffusion of fluid between the sample chamber and the hydration chamber through the membrane. Loading chambers according to embodiments of the present invention can be used to concentrate a protein sample solution prior to electrophoresis.

In further embodiments, methods for staining an electrophoresis cassette include providing an electrophoresis cassette comprising first and second opposing plates. An electrophoresis medium and a membrane layer on the electrophoresis medium are provided between the first and second opposing plates such that a void is formed between the membrane layer and the first opposing plate. Electrophoresis separation of a sample solution is conducted using the electrophoresis medium. A staining reagent is applied to the electrophoresis medium through the void between the membrane layer and the first opposing plate. A staining solution may be automatically injected into the cassette, and therefore, it may be unnecessary to remove the electrophoresis medium and manually apply the stain.

DETAILED DESCRIPTION OF THE INVENTION

Figure 1:
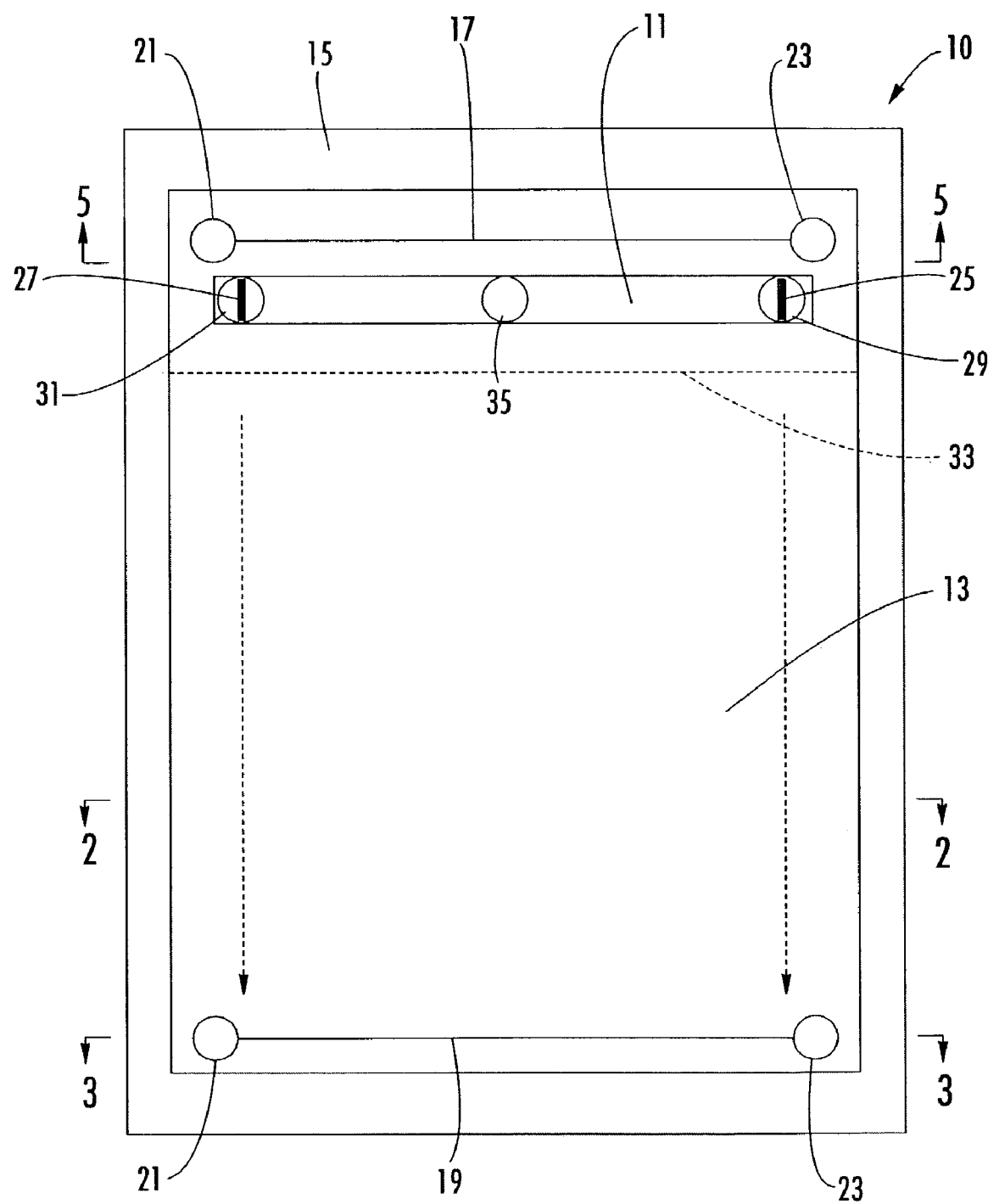
FIG. 1 is a view of the top side of a 2-D PAGE device according to embodiments of the present invention.

The present invention now will be described more fully hereinafter with reference to the accompanying drawings, in which illustrative embodiments of the invention are shown. This invention, however, should not be construed as limited to the embodiments set forth herein; rather, these embodiments are provided so that this disclosure will be thorough and complete, and will fully convey the scope of the invention to those skilled in the art.

In the drawings, the relative sizes of elements may be exaggerated for clarity. When an element is described as being on or adjacent another element, the element may be directly on or adjacent the other element, or other elements may be interposed therebetween. In contrast, when an element is referred to as being "directly on" another element, there are no intervening elements present. Like reference numerals in the drawings denote like members.

For ease of discussion, the exemplary embodiments disclosed herein may refer to IPG strip and polyacrylamide gel electrophoresis media. As would be appreciated by those of skill in the art, other electrophoresis media are interchangeable with IPG strips and polyacrylamide gels. Other acrylamide gels that may be used include gel media available from Invitrogen,™ Carlsbad, Calif. (U.S.A.) such as NuPAGE™ Bis-Tris (separation range 1.5 to 300 kDa), NuPAGE™ Tris-Acetate (separation range 30 to 400 kDa), Novex™ Tris-Glycine (separation range 6 to 500 kDa), Tricine (separation range 2 to 200 kDa), and Zymogram (separation range 30 to 200 kDa).

Figure 2:
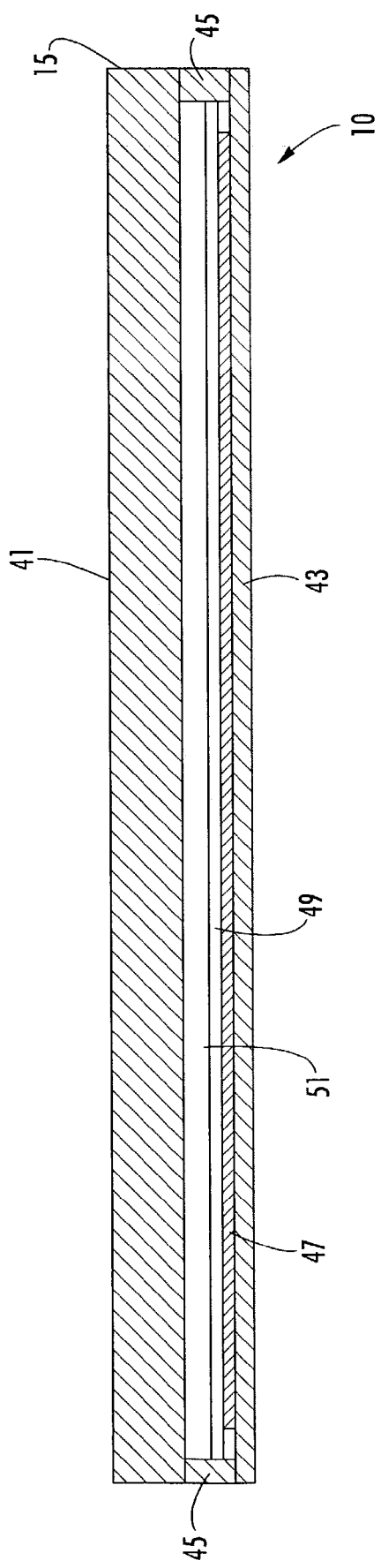
FIG. 2 is a cross-sectional view of the 2-D PAGE device of FIG. 1.

A 2-D PAGE device 10 is shown in FIGS. 1 and 2. The device 10 includes cassette housing 15, which supports an IPG strip region 11 and a polyacrylamide gel region 13. The cassette housing 15 can be about 8 cm long and about 8 cm wide. A sample solution can be introduced into the device 10 through a sample opening 35 and onto the IPG strip region 11. IPG strips are commercially available under several trade names including BioRad™ from BioRad Laboratories, Hercules, Calif., U.S.A.

An IPG strip may be inserted into IPG strip region 11. An IPG strip typically has a shelf life of about one year and should be kept dry and either refrigerated or frozen to increase shelf life. Therefore, it may be advantageous to store IPG strips separately from the cassette housing 10, and to load and hydrate an IPG strip in the IPG strip region 11 just prior to performing electrophoresis. The IPG electrodes 25 and 27 can be used to apply the current to the IPG strip region 11 such that an IPG strip can perform isoelectric focusing to a sample added to an IPG strip through the sample opening 35.

A protein sample may be loaded onto an IPG strip placed in the IPG strip region 11 using a "cup loading" method in which the sample is placed in a cup that interfaces with the hydrated IPG strip. Drip rods may also be used to load the sample as follows. Upon rehydration of the IPG strip, a protein sample may be placed into a drip rod that is then placed on the surface of the IPG strip. The drip rod can contact the IPG strip through the sample openings 35 or buffer openings 31. The sample may be diluted, for example, by dissolving the sample in one or more of 9.5 M urea, 2–4% non-ionic or zwitterionic detergent, 1% Dithiothreitol (DTT), and 0.8% carrier ampholyte. See O'Farrell PH (1975) "High resolution two-dimensional electrophoresis of proteins." J Biol Chem 250: 4007–4021. Relatively hydrophobic proteins may be dissolved by a mixture of 2 M thiourea and 7 M urea instead of 9.5 M urea and/or other detergents. See Rabilloud T, Adessi, C, Giraudel A, Lunardi J (1997) "Improvement of the solubilization of proteins in two-dimensional electrophoresis with immobilized pH gradients." Electro-phoresis 18: 307–316.

Isoelectric focusing typically requires exposing a sample solution to an IPG strip at about 15 degrees C. for about 12 hours at a constant voltage of about 300 V. Alternatively, various voltages may be applied depending on the IPG strip used and the proteins to be focused. For example, an eleven centimeter IPG strip can be focused for thirty minutes at 250 volts, sixty minutes of slow ramping to 8,000 volts, followed by fifteen to twenty kilovolt hours at 8,000 volts.

A polyacrylamide gel 47 (FIG. 2), such as Tris-Glycine acrylamide, extends in a substantially flat planer two dimensional slab in the polyacrylamide gel region 13 (FIG. 1). A removable dam 33 separates the IPG region 11 from the polyacrylamide gel region 13. The removable dam 33 can be plexiglass. In operation, the removable dam 33 can be used to prevent spillage of a high salt content polyacrylamide gel 47 into the IPG strip region 11 while buffers can flush the IPG strip. Preferably, the total salt concentration should not exceed 300 mM in a sample. The removable dam 33 can be inserted between the opposing plates 41 and 43 of the cassette housing 10 by cutting an incision in the top opposing plate 41. A plexiglass removable dam 33 can be inserted in the incision and sealed with a high resistance vacuum sealant. The removable dam 33 can be removed prior to performing electrophoresis on the polyacrylamide gel 47. After removal of the dam 33, the incision can be sealed, for example, with sequencing tape. However, the removable dam 33 may not be necessary to separate the IPG strip region 11 from the polyacrylamide gel region 13. For example, the cassette housing 10 may be placed at an angle to prevent a buffer from coming in contact with the polyacrylamide gel 47. PAGE electrodes 17 and 19 in the form of metal filaments can be used to apply a voltage across the polyacrylamide gel region 13. After proteins from a sample are focused on an IPG strip placed in the IPG strip region 11, the protein from the IPG strip can be transferred from the IPG strip to the polyacrylamide gel region 13. This transfer can be facilitated by a suitable buffer, which can be applied through the buffer openings 29 and 31. As described above, an SDS/buffer can be used to increase the solubility and to impart a negative charge to the proteins in the solution. Other suitable buffers can be used such as dithiothreitol, tributyl phosphine, a mixture of 6M urea, 0.375 M Tris pH 8.8, 2% SDS, 20% glycerol, or 2% (w/v) Dithiothreitol (DTT), or a mixture of 6M urea, 0.375 M Tris pH 8.8, 2% SDS, 20% glycerol, or 2% (w/v) iodoacetamide. After adding a buffer through buffer openings 29 and 31, a stopper such as a cylindrical piece of filter paper may be placed in the buffer openings 29 and 31. Purified water can be added to the filter paper stopper so that the stopper can serve as a salt sink to remove impurities.

Once the dam 33 is removed and a buffer applied to the sample, an electric current is applied to the PAGE electrodes 17 and 19 so that the proteins that were isoelectrically focused on an IPG strip can travel towards the anode electrode 19. As a result, the proteins in the sample are separated by their molecular weight in the polyacrylamide gel region 13. Separation of the proteins in a sample by molecular weight along the polyacrylamide gel typically takes between about 30 and 40 minutes at ambient temperature. As understood by those of skill in the art, bromophenol Blue Dye can be used to determine the length exposure needed.

The IPG electrodes 25 and 27 can be connected to a current source (not shown) through buffer openings 29 and 31, and PAGE electrodes 17 and 19 can be connected to current sources through electrode openings 21 and 23. As will be appreciated by one of skill in the art, buffer openings 29 and 31, electrode openings 21 and 23, and sample openings 35 can be placed at other locations around housing 15. For example, the sample opening 35 is preferably in the center of the IPG strip region 11, but can also be situated off-center or at one end of the IPG strip region 11. Although the IPG electrodes 25 and 27 should be placed at opposite ends of the IPG region 11, additional buffer openings can be placed at various points along the IPG region 11. The buffer openings 29 and 31, electrode openings 21 and 23 and the sample opening 35 can be used to introduce various fluids into the cassette such as buffers, hydration solutions, sample solutions and staining reagents. These fluids may be introduced manually or automatically.

As can be seen in FIG. 2, the cassette housing 15 includes two opposing plates 41 and 43. Spacers 45 separate opposing plates 41 and 43. The polyacrylamide gel 47 forms a layer on one of the opposing plates 34. A semi-permeable dialysis membrane 49 extends over top of the polyacrylamide gel 47. The semi-permeable membrane 49 encloses and surrounds the polyacrylamide gel 47 to define a void 51 in between the membrane 49 and the other of the opposing plates 41. The semi-permeable membrane can prevent the polyacrylamide gel 47 from expanding or moving into the void 51. In certain embodiments, the polyacrylamide gel 47 and the membrane 49 can be chemically crosslinked together.

Figure 3:
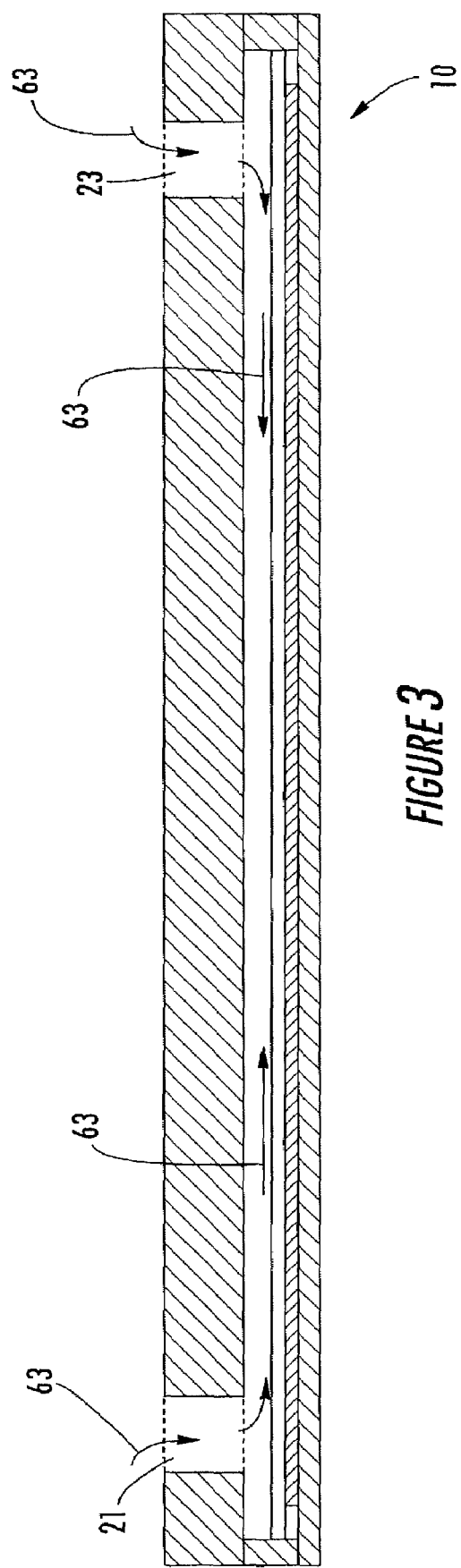
FIG. 3 is a cross-sectional view of the 2-D PAGE device of FIG. 1 shown illustrating the flow channels for buffer solutions or staining reagents.

The void 51 that is defined by the membrane 49 can provide a space in which fluids may be introduced onto the polyacrylamide gel 47. For example, as can be seen in FIG. 3, a staining reagent may be introduced by electrode openings 21 and 23. The staining reagent can flow along arrows 63 across the membrane 49 and onto the polyacrylamide gel 47. Staining reagents typically require about ninety minutes to stain a polyacrylamide gel. Therefore, embodiments of the present invention can provide staining inside the cassette and may eliminate the need to remove the polyacrylamide gel from the cassette housing 15 for staining. Alternatively, the polyacrylamide gel 47 can be removed from the housing 10 and subsequently stained.

Many of the steps described herein may be automated, reducing the need for skilled operators to perform the steps manually. For example, staining can be accomplished by automatically adding a staining reagent into the cassette such as with a machine configured to release the staining reagent into the electrode openings 21 and 23 at a predetermined time. As would be understood by those of skill in the art, the application of voltage on an IPG strip or polyacrylamide gel, the application of a buffer, the removal of the dam 33, and the application of the staining reagent are examples of steps that may each be automated. For example, mechanical systems can be controlled by software and configured using known techniques to apply a solution through a specified opening in the cassette housing 15, apply a voltage to a specified electrode, or remove the dam 33, at predetermined times in order to perform 2-D PAGE. Automation of one or more of the steps may produce 2-D PAGE results with higher reproducibility and accuracy and require less intervention from a skilled operator.

The two opposing plates 41 and 43 and the spacers 45 can be formed of a single unitary member or, alternatively, from a plurality of parts. For example, the opposing plates 41 and 43 may be separately molded pieces that are joined by molded spacers 45. Preferably the housing 15 is a plastic housing that is heat resistant. However, glass or other suitable materials may also be used. In certain embodiments, the spacers 45 can define an opening that is about 2 mm in height.

A loading device 110 that can be used to concentrate protein samples is shown in the FIGS. 4A–4C and FIG. 5. The loading device 110 includes a sample chamber 111 and two hydration chambers 113A and 113B adjacent the sample chamber 111. The hydration chambers 113A and 113B are separated from the sample chamber 111 by semi-permeable membranes 117A and 117B. A sample solution 121 including proteins 123 can be placed in the sample chamber 111 through opening 127. The sample chamber 111 includes a second opening 115, which is closed when the sample 121 is placed in the sample chamber 111 in FIG. 4B.

Figure 4A:
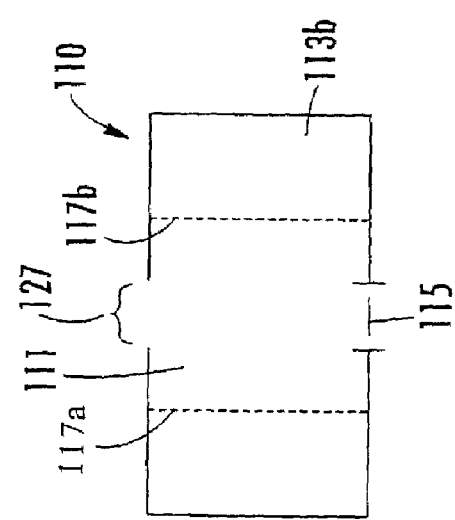
FIG. 4A–4C is a cross-sectional view of a loading device according to embodiments of the present invention.
Figure 4B:
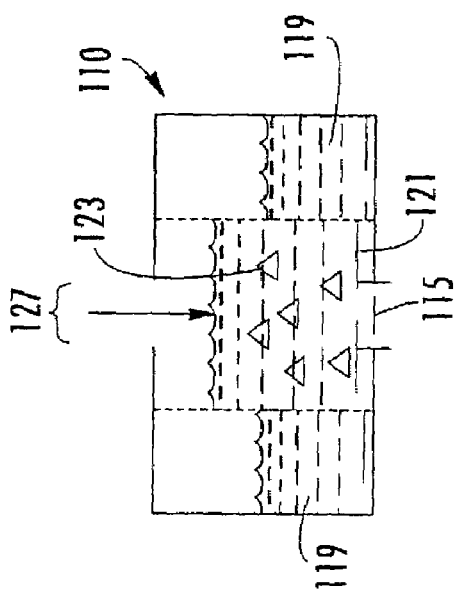

The hydration chambers 113A and 113B are filled with a hypertonic solution 119 in FIG. 4B. The solution 119 is hypertonic with respect to the protein sample solution 121. Therefore, turgor pressure increases in the hydration chambers 113A and 113B when the sample chamber 111 is filled with the protein solution 121. As a result, electrolytes from the sample solution 121 flow into hydration chambers 113A and 113B by way of membranes 117A and 117B, and the protein sample solution 121 is concentrated as can be seen in FIG. 4C.

Figure 4C:
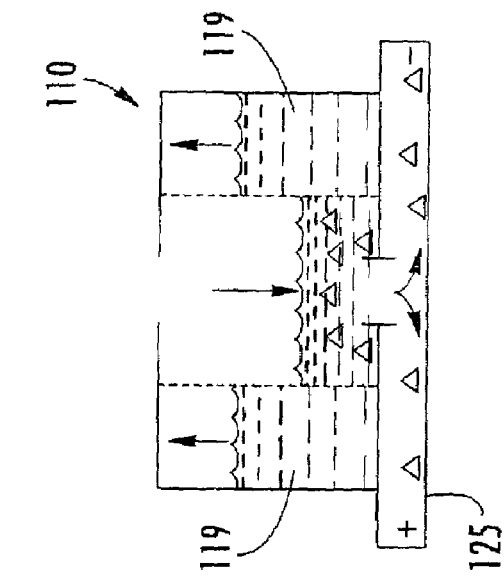
Figure 5:
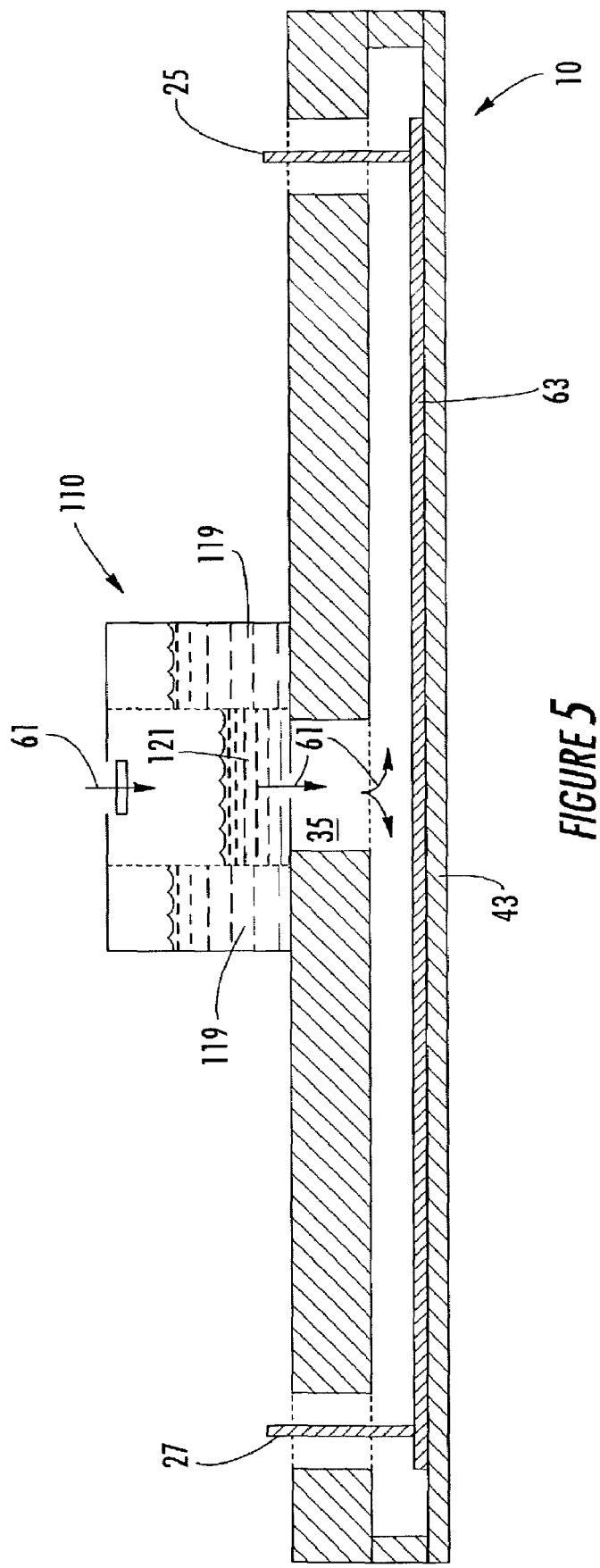
FIG. 5 is a cross-sectional view of the 2-D PAGE device of FIG. 1 shown with the loading device of FIG. 3.

As shown in FIG. 4A–C, the opening 115 to the sample chamber 111 can be closed to allow concentration of the sample solution (FIGS. 4A–B), and subsequently opened such that the sample solution 121 can flow into an electrophoresis separation medium, such as an IPG strip 125 (FIG. 4C). As can be seen in FIG. 5, the loading device 110 can be used to load a sample solution 121 into the electrophoresis device 10. The sample solution 123 follows arrows 61 onto IPG strip 63 through the opening 115 and the sample opening 35. The loading device 110 can be used to provide automated loading of a concentrated solution into the electrophoresis device 10.

In the drawings and specification, there have been disclosed typical illustrative embodiments of the invention and, although specific terms are employed, they are used in a generic and descriptive sense only and not for purposes of limitation, the scope of the invention being set forth in the following claims.

That which is claimed is:

1. A device for two-dimensional electrophoresis comprising:
    a cassette comprising two opposing plates, the two opposing plates forming a first elongated portion for receiving a first elongated electrophoretic separation medium and a second portion extending away from the first portion;
    a second electrophoretic separation medium on the second portion and between the two opposing plates; and
    a dialysis membrane extending across the second electrophoretic separation medium,
    wherein the dialysis membrane is crosslinked to the electrophoretic separation medium.

2. The device of claim 1, further comprising a staining reagent between the opposing plates.

3. The device of claim 1, further comprising a molded spacer along an outer rim of the two opposing plates.

4. The device of claim 1, wherein one of the two opposing plates has an aperture for inserting a sample between the two opposing plates onto the first elongated portion.

5. The device of claim 1, wherein the first electrophoresis medium comprises an immobilized pH gradient gel (IPG) strip.

6. The device of claim 1, wherein the second electrophoresis medium comprises Tris-Glycine acrylamide gel.

7. The device of claim 1, further comprising a buffer aperture for applying a buffer to the first elongated portion of the cassette.

8. The device of claim 1, further comprising a buffer aperture for applying a buffer to the second portion of the cassette.

9. The device of claim 1, further comprising first and second pairs of electrodes, the first pair of electrodes configured to apply a current to the first elongated portion of the cassette and the second pair of electrodes configured to apply a current to the second portion of the cassette.

10. The method of claim 1, wherein the dialysis membrane is in direct contact with the second electrophoretic medium.

11. A device for two-dimensional electrophoresis comprising:

a cassette comprising two opposing plates, the two opposing plates forming a first elongated portion for receiving a first elongated electrophoretic separation medium and a second portion extending away from the first portion;

a second electrophoretic separation medium on the second portion and between the two opposing plates; and a dialysis membrane extending across the second electrophoretic separation medium;

wherein the second electrophoresis medium is deposited on one of the plates and the dialysis membrane defines a void between the dialysis membrane and the other of the two opposing plates.

12. The device of claim 11, further comprising a staining reagent applied to the second electrophoresis medium through the void between the dialysis membrane and one of the two opposing plates.

* * * * *